United States Patent

Commandeur et al.

[11] Patent Number: 5,601,755
[45] Date of Patent: Feb. 11, 1997

[54] DIELECTRICS COMPRISING METHYL/BENZYL DERIVATIVES OF DIPHENYLMETHANE

[75] Inventors: Raymond Commandeur, Vizille; Noelle Berger, Ecully; Pierre Jay, Saint-Didier Au Mont D'Or, all of France

[73] Assignee: Atochem, Puteaux, France

[21] Appl. No.: 399,998

[22] Filed: Mar. 6, 1995

Related U.S. Application Data

[63] Continuation of Ser. No. 216,507, Mar. 22, 1994, abandoned, which is a continuation of Ser. No. 959,347, Oct. 13, 1992, abandoned, which is a continuation of Ser. No. 661,228, Feb. 27, 1991, abandoned.

[30] Foreign Application Priority Data

Feb. 27, 1990 [FR] France ................................. 90 02421

[51] Int. Cl.$^6$ ................... C07C 1/16; C07C 2/02; C07C 15/16; H01B 3/22
[52] U.S. Cl. ................. 252/570; 252/581; 585/25; 585/19; 174/25 C; 174/23 C
[58] Field of Search ..................... 252/570, 581; 585/25, 19; 174/25 C, 23 C

[56] References Cited

U.S. PATENT DOCUMENTS

| | | | |
|---|---|---|---|
| 4,189,391 | 2/1980 | Kimura et al. | 252/570 |
| 4,493,943 | 1/1985 | Sato et al. | 174/25 C |
| 4,902,841 | 2/1990 | Kawakami et al. | 585/25 |

FOREIGN PATENT DOCUMENTS 0299867  1/1989  European Pat. Off. .

*Primary Examiner*—Paul Lieberman
*Assistant Examiner*—Necholus Ogden
*Attorney, Agent, or Firm*—Burns, Doane, Swecker & Mathis, L.L.P.

[57] ABSTRACT

Novel dielectric liquids for such electrical components as transformers, capacitors and cables, especially adopted for low temperature applications, comprise immixtures of benzyltoluene, (methylbenzyl)toluene, benzylxylene and (methylbenzyl)xylene, and optionally include the benzyl or methylbenzyl derivatives thereof; these immixtures are facilely prepared by chlorinating a mixture of xylene and toluene and then adding a catalytically effective amount of a Friedel-Crafts catalyst to the medium of chlorination.

32 Claims, No Drawings

DIELECTRICS COMPRISING METHYL/BENZYL DERIVATIVES OF DIPHENYLMETHANE

This application is a continuation, of application Ser. No. 08/216,507, now abandoned, filed Mar. 22, 1994; which is a continuation of Ser. No, 07/959,347, now abandoned, filed Oct. 13, 1992; which is a continuation of Ser. No. 07/661,228, now abandoned, filed Feb. 27, 1991.

BACKGROUND OF THE INVENTION

1. Field of the Invention

The present invention relates to novel compositions based on methyl and benzyl derivatives of diphenylmethane and to the use of such compositions as dielectric fluids.

2. Description of the Prior Art

European Patent 136,230 describes dielectrics which remain liquid at low temperatures without displaying high viscosity.

SUMMARY OF THE INVENTION

A major object of the present invention is the provision of novel dielectric compositions which remain liquid at even lower temperatures than those heretofore characterizing the state of the art.

Another object of the present invention is the provision of novel dielectric compositions which can be used in voltage transformers, and thus which exhibit a high breakdown voltage.

Briefly, the present invention, features novel dielectric compositions comprising benzyltoluene, benzylxylene, (methylbenzyl)toluene and (methylbenzyl)xylene.

DETAILED DESCRIPTION OF THE PREFERRED EMBODIMENTS OF THE INVENTION

More particularly according to the present invention, by the term "benzyltoluene" is intended an isomer or mixture of isomers of the formula:

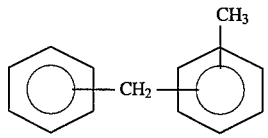

By the term "benzylxylene" is intended an isomer or mixture of isomers of the formula:

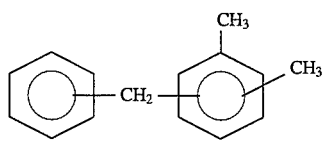

By the term "(methylbenzyl) toluene" is intended an isomer or mixture of isomers of the formula:

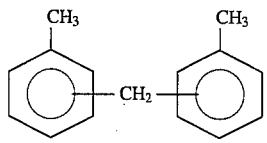

And by the term "(methylbenzyl)xylene" is intended an isomer or mixture of isomers of the formula:

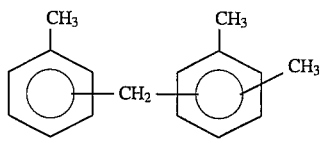

The compositions according to the invention also preferably comprise an isomer or mixture of isomers of the formula (A):

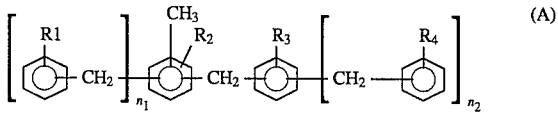

in which $R_1$, $R_2$, $R_3$ and $R_4$, which may be identical or different, are each a hydrogen atom or a methyl radical, and $n_1$ and $n_2$ are each 0, 1 or 2, with the proviso that $n_1+n_2$ is greater than or equal to 1 and less than or equal to 3.

When $R_1$ to $R_4$ are hydrogen and $n_1+n_2=1$, product (A) is a dibenzyltoluene. However, product (A) can also comprise a mixture of isomers containing those compounds in which $n_1+n_2=1$, $n_1+n_2=2$ and $n_1+n_2=3$.

It is also within the scope of the invention if the subject compositions additionally comprise triphenylmethanes which may be substituted by methyl, benzyl and methylbenzyl radicals. Exemplary such substituted triphenylmethanes include ditolylphenylmethane, dixylylphenylmethane and even xylyltolylphenylmethane.

The compositions according to the invention are dielectrics, for example for capacitors, transformers, or even electric cables.

For dielectric applications, it is advantageous to purify the compositions of the invention using bleaching earths, zeolites, etc., followed by adding antioxidants or acid acceptors thereto, such as epoxides. Such conditioning treatments are known to this art and are described, for example, in European Patents Nos. 8,251 and 136,230, hereby expressly incorporated by reference.

It too is within the scope of this invention for the subject compositions to be in admixture with other dielectrics, for example tetrachlorobenzyltoluenes, chlorobenzenes or chlorotoluenes described in European Patent No. 8,251 or mixed with the mineral oils typically used in transformers.

Compositions comprising at least 60 parts by weight of compounds having two benzene ring members (i.e., benzyltoluene, benzylxylene, (methylbenzyl)toluene and (methylbenzyl)xylene) per 40 parts by weight of isomers of the formula (A) are particularly advantageous.

In a preferred embodiment of the invention, of the four compounds having two benzene rings, benzyltoluene constitutes at least 30% by weight of the total weight of these four compounds, advantageously 50%, and preferably 70% by weight.

Particularly preferred compositions are those in which the amount of the four compounds having two ring members ranges from 65 to 90 parts by weight per 35 to 10 parts by weight of isomers of the formula (A), respectively.

The different compounds or isomers of the compositions according to the invention, i.e., the methylated and benzylated derivatives of diphenylmethane, can be prepared via different techniques and then admixed. However, this invention also features a particularly simple process for preparing the subject compositions.

Indeed, in European Patents Nos. 136,230 and 299,867, assigned to the assignee hereof, the preparation of benzyltoluene and (methylbenzyl)xylene is described. In published European Patent Application No. 282,083, the preparation of a mixture of benzyltoluene and (methylbenzyl)toluene by alkylation and transalkylation reactions at high temperature, which have to be followed by complex purifications, are described. The process according to the invention is characterized in that, in a first step thereof, a partial free-radical chlorination of a mixture of toluene and xylene is carried out, followed by a second step which comprises contacting the mixture resulting from the first step with a Friedel-Crafts catalyst.

The free-radical chlorination of the mixture of toluene and xylene is typically carried out at a temperature ranging from 50° to 110° C. and preferably from 70° to 100° C. It is preferably conducted in such manner that only 10% to 30%, expressed as a molar percentage, of the mixture is converted into the corresponding chlorinated derivative. As regards the generator of the free radicals, either a photochemical initiator or a chemical initiator can be employed; exemplary chemical initiators include the azo compounds, such as azodiisobutyronitriie or azodivaleronitrile, or peroxides, such as lauroyl peroxide. The amount of chemical initiator used generally ranges from 0.05% to 3% by weight, relative to the weight of the mixture, and preferably from 0.1% to 1.5%.

The chlorination has to be partial, i.e., at the end of this first step, xylene and toluene must remain in the reaction mixture. The initial amount of toluene and xylene, i.e., prior to the chlorination, can be as desired; the more benzyltoluene is desired, the higher the amount of toluene. The second step comprises contacting the above mixture with a catalytically effective amount of a Friedel-Crafts catalyst. Such catalysts are also per se known to this art.

These catalysts include, for example, the inorganic halides and the mineral acids. In actual practice, this reaction is advantageously carried out at a temperature ranging from 30° to 110° C., and preferably from 50° to 100° C. Exemplary inorganic halides include ferric chloride, antimony trichloride, titanium tetrachloride and aluminum chloride; these are advantageously used in weight ratios typically ranging from 50 ppm to 1% and preferably from 100 ppm to 0.5%, relative to the reaction medium. One example or a suitable mineral acid is sulfuric acid, used, for example, at a concentration ranging from 70% to 95% by weight. It is also possible to employ zeolites, or else certain inorganic oxides.

The catalyst is advantageously added to the mixture resulting from the first step.

Upon completion of the second step, which is in fact a condensation reaction, it is advantageous, after distilling off the excess toluene and xylene, to continue with the removal of the catalyst by any known technique, such as washing with water, neutralization, drying, etc.

A simple distillation then suffices to recover the compositions of the invention. It is also possible to separate the four compounds having two ring members from products (A) and any higher products separated by distillation. The reaction mixture obtained immediately after condensation, essentially comprising methylated and benzylated derivatives of diphenylmethane and possibly excess xylene and toluene, may also contain chlorinated organic compounds, such as:

(i) chlorinated xylenes of the formula:

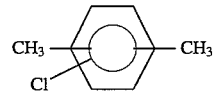

(ii) chlorotoluenes of the formula:

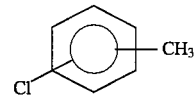

(iii) (methylchlorobenzyl) xylene:

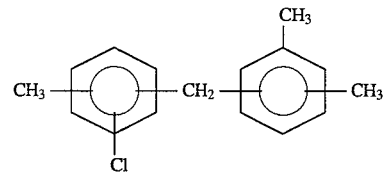

and, in general, methylated and benzylated derivatives of diphenylmethane bearing one or more chlorine atoms on the benzene ring. These compounds have been formed from chlorine and xylene and toluene, and possibly the Friedel-Crafts catalyst, when the product is a chloride. For certain applications, it is desirable that the compositions of the invention contain very little or no chlorine whatsoever. In a preferred embodiment of the invention, the methylated and benzylated derivatives of diphenylmethane are treated in order to remove the chlorinated organic compounds therefrom. It is advantageous to carry out such treatment after the removal of excess xylene, toluene and the catalyst.

Thus, after the condensation reaction, excess xylene and toluene and then the catalyst are removed, and the organic chlorine is next removed from this crude mixture of methylated and benzylated derivatives of diphenylmethane.

Any process for destroying chlorinated organic compounds may be employed, for example the process described in European Patent No. 306,398, using an alkali metal alcoholate, or the process described in European Patent No. 250,748, using a higher alcoholate. It is preferred to employ the dechlorination process described in European Patent No. 306,398.

In another preferred embodiment of the invention, the crude mixture is contacted with an alcoholate and the entire mixture is heated to a temperature ranging from 220° to 320° C., with stirring. The alcoholate is preferably a sodium alcoholate, for example sodium methoxide.

After the dechlorination treatment, a simple distillation is sufficient for recovering the methylated and benzylated derivatives of diphenylmethane which have a low chlorine content. A heavy fraction containing the remainder of the dechlorinating agent, an alkali metal chloride (NaCl) and higher oligomers is recovered as a tail fraction, or bottoms.

It is also within the scope of the invention to recycle such heavy fraction obtained as a tail fraction, whether partially or entirely, and if the latter fraction were to be used either alone or in admixture with the product used for destroying the chlorinated organic products.

It too is within the scope of the invention, after the condensation reaction and removal of xylene and toluene, to recycle the compounds having two ring members (benzyltoluene, benzylxylene, (methylbenzyl)xylene, (methylbenzyl)toluene, either partially or entirely, back into the condensation step. The advantage of such recycling is to increase the proportion of the compounds of formula (A). After their removal, the xylene and toluene can be reused upstream in the process. All or a portion of the compounds having two ring members could also be withdrawn after the dechlorination and recycled to the condensation step.

It is also within the scope of the invention to mix benzyl chloride, methylbenzyl chloride ($CH_3C_6H_4CH_2Cl$), xylene and toluene, and to carry out the condensation reaction of the second step using this mixture, by adding the Friedel-Crafts catalyst thereto.

Moreover, it has also been found that, if the process of the invention is carried out using ferric chloride as the Friedel-Crafts catalyst, it is not necessary to remove the catalyst, i.e., the mixture obtained after the condensation reaction can be distilled to first obtain xylene, toluene, then the four products having two ring members and products (A); all such compositions are suitable for use as dielectrics. This, however, is not the case when using aluminum chloride; if the ammonium chloride is not removed after the condensation, very frequently the mixture cannot be distilled. If the products can in fact be recovered, they are then unsuitable for use as dielectrics. It has also been found that the use of ferric chloride as the condensation catalyst not only permits avoiding any required removal thereof, but also the ultimate destruction of the chlorinated organic compounds, as described above, can be carried out as soon as the condensation reaction is complete. Nevertheless, it is recommended to remove the excess xylene and toluene as soon as the condensation reaction is complete.

After the dechlorination treatment, a simple distillation is sufficient to recover the four products having two ring members and products (A) which have a low chlorine content. A heavy fraction which contains the remainder of the dechlorinating agent, alkali metal chloride, iron salts and higher oligomers is obtained as a tail fraction. As described above, this heavy fraction can be recycled and used as make-up solution for the dechlorinating agent.

In order to further illustrate the present invention and the advantages thereof, the following specific examples are given, it being understood that same are intended only as illustrate and in nowise limitative.

EXAMPLE 1

Into a reactor equipped with a stirrer, a condenser, a chlorine introduction tube and a 30-watt Philips Tladk lamp, the following materials were introduced:
(i) 40 mol of toluene (3680 g);
(ii) 3.25 mol of ortho-xylene (344.5 g); and 10.8 mol of
(iii) gaseous chlorine were then introduced at a temperature of 100° C. over a period of time of 2 hours, 40 minutes.

After photochemical initiation had been discontinued and the reaction medium had been degassed with nitrogen, it was placed into a dropping funnel and introduced over a period of time of 2 hours into a reactor equipped with a stirrer and containing:
(a) 42.36 tool of toluene (3897 g);
(b) 3.44 tool of ortho-xylene (364 g); and
(c) 2.1 g of $FeCl_3$.

The reaction temperature was 100° C. An additional 1.3 g of $FeCl_3$ was added, and the temperature was maintained for another 2 hours while degassing with nitrogen. Excess toluene and ortho-xylene were removed by distillation under a vacuum of 15 mm of mercury using a column provided with a few plates. The residue was then treated with 2.2% of sodium methoxide under a blanket of nitrogen in a stirred reactor at 290° C. for 5 hours. The mixture resulting from this treatment was subjected to distillation in a column provided with a few plates under 0.5 mm of mercury, to give:

(1) A fraction of a colorless liquid which distilled at a temperature of 110° to 125° C. and which had the following composition:
Benzyltoluene : 71.6%
(Methylbenzyl) toluene : 13.2%
Benzylxylene : 12.5%
(Methylbenzyl) xylene) : 2.7%

(2) A fraction of a clear oily yellow liquid which distilled at a temperature of 190° to 200° C. and which comprised a mixture of type (A) compounds in which $n_1+n_2$ was equal to 1. The dibenzyltoluene content of this fraction was about 50%.

The first fraction constituted 1,200 g and the second 300 g. About 60 g of a mixture of heavy residues remained.

EXAMPLE 2

Crystallization tests were carried out using the following:
(a) A liquid designated BTXX, according to the invention, containing:
   (i) 83 parts of the 1st fraction from Example 1;
   (ii) 17 parts of the 2nd fraction from Example 1 (i.e., a mixture of 14 parts of type (A)/$n_1+n_2=1$ compounds and 3 parts of triphenylmethane derivatives)
(b) A liquid designated BT06, not according to the invention, described in European Patent No. 136,230 and containing:
   (i) 79 parts of benzyltoluene;
   (ii) 16 parts of dibenzyltoluene, (i.e., product (A) of the present invention in which $R_1$ to $R_4$ are H and $n_1=n_2=1$); and
   (iii) 4 parts of ditolylphenylmethane.

The tubes containing BT06 and BTXX were maintained at −50° C. for 43 days. They had been seeded with benzyltoluene crystals.

⅔ of BT06 were crystallized at −45° C., while the BTXX remained liquid.

At −50° C., BTXX was still liquid.

After stirring at −50° C., BT06 had a significant amount of crystals while BTXX remained liquid.

EXAMPLE 3

Measurement of dielectric strength:
The measurements were carried out using an alternating current of 50 Hz and at ambient temperature, employing electrodes ϕ=0.6 mm and Rogowski disc ϕ=40 mm. The voltage was applied stepwise with an increase of 1,000 volts every 30 seconds.

| Distance between | Breakdown voltage | |
|---|---|---|
| the electrodes | BTXX | PXE |
| 3.2 mm | 54.6 | 40.2 |
| 10 mm | 72.0 | 63.3 |

The values are reported in kilovolts and are the average of 5 measurements.

BTXX is the designation for the composition according to the invention as indicated in Example 2.

PXE is the designation for a dielectric not according to the invention, i.e., a mixture of 1-phenyl–1xylylethane isomers of the formula:

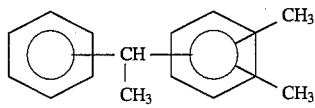

While the invention has been described in the terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter adopted for dielectric application, comprising an immixture having a dielectrically effective amount of benzyltoluene, benzylxylene, (methylbenzyl)toluene and (methylbenzyl)xylene, which does not have a significant amount of crystals at a temperature of −45° C., further comprising at least 10% by weight of an isomer or isomers of the formula (A);

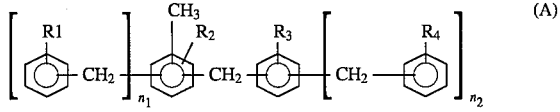

in which $R_1$, $R_2$, $R_3$ and $R_4$, which may be identical or different, are each a hydrogen atom or a methyl radical and $n_1$ and $n_2$ are each 0, 1 or 2, with the proviso that $n_1+n_2$ is greater than or equal to 1 and less than or equal to 3, and comprising at least 60 parts by weight of said immixture of toluene/xylene compounds, and further wherein said benzyltoluene comprises at least 70% by weight of said immixture of toluene/xylene compounds.

2. The composition of matter as defined by claim 1, wherein benzyltoluene comprises at least 30% by weight of said immixture of toluene/xylene compounds.

3. The composition of matter as defined by claim 2, wherein benzyltoluene comprises at least 50% by weight of said immixture of toluene/xylene compounds.

4. The composition of matter as defined by claim 1, further comprising a triphenylmethane.

5. The composition of matter as defined by claim 2, further comprising a triphenylmethane.

6. The composition of matter as defined by claim 1, further comprising a bleaching earth, zeolite, antioxidant, acid acceptor, or mixture thereof.

7. The composition of matter as defined by claim 1, further comprising a tetrachlorobenzyltoluene, chlorobenzene, chlorotoluene or mineral oil.

8. The composition of matter as defined by claim 1, further comprising a chloroxylene or (methylchlorobenzyl)xylene.

9. A process for the preparation of the composition of matter as defined by claim 1, comprising first partially free-radical chlorinating an admixture of toluene and xylene, and next condensing the resulting medium of partial chlorination in the presence of a catalytically effective amount of a Friedel-Crafts catalyst.

10. The process as defined by claim 9, comprising chlorinating from 10 to 30 mole % of said admixture of toluene and xylene.

11. The process as defined by claim 9, further comprising reacting the organic chlorinated compounds present in the medium of condensation with sodium or an alkali metal alcoholate.

12. The process as defined by claim 9, further comprising recycling at least a fraction of the reaction products having two benzene ring members to said condensation reaction.

13. The process as defined by claim 11, comprising distilling the final medium of reaction to obtain a heavy fraction therefrom and at least partially recycling such heavy fraction to said organic chlorinated compound reaction.

14. The process as defined by claim 14, wherein ferric chloride comprises said Friedel-Crafts catalyst.

15. The process as defined by claim 14, comprising reacting said organic chlorinated compounds without removing any ferric chloride from the medium of condensation.

16. In an electrical component including a dielectric liquid, the improvement which comprises, as the dielectric liquid therefor, a dielectrically effective amount of the composition of matter as defined by claim 1.

17. In an electrical component including a dielectric liquid, the improvement which comprises, as the dielectric liquid therefor, a dielectrically effective amount of the composition of matter as defined by claim 2.

18. The electrical component as defined by claim 16, comprising a capacitor, transformer or cable.

19. The composition of matter as defined by claim 1, wherein the amount of said benyzltoluene, benzylxylene, (methybenzyl)toluene and (methybenyzl)xylene is sufficient to result in a dielectric material which does not have a significant amount of crystals at a temperature of −50° C.

20. An electrical process which uses an electrical component including a dielectric liquid wherein the improvement comprises, using as the dielectric liquid, a dielectrically effective amount of the composition as defined by claim 1.

21. The process of claim 20, wherein the process is conducted at low temperatures.

22. An electrical process which uses an electrical component including a dielectric liquid wherein the improvement comprises, using as the dielectric liquid, a dielectrically effective amount of the composition as defined by claim 1.

23. The process of claim 22, wherein the process is conducted at low temperatures.

24. A composition of matter adopted for dielectric application, consisting essentially of an immixture of benzyltoluene, benzylxylene, (methylbenzyl)toluene and (methylbenzyl)xylene.

25. The composition of claim 24, wherein the amounts of benzyltoluene, benzylxylene, (methylbenzyl)xylene are in amounts sufficient to result in a dielectric material which does not have a significant amount of crystals at a temperature of −45° C.

26. The composition of claim 25, wherein the amount of said benzyltoluene, benzylxylene, (methylbenzyl)toluene and (methylbenzyl)xylene is sufficient to result in a dielectric material which does not have a significant amount of crystals at a temperature of −50° C.

27. A composition of matter adopted for dielectric applications, consisting essentially of benzyltoluene, benzylxylene, (methylbenzyl)toluene and (methylbenzyl)xylene and further comprising at least one isomer of the formula (A):

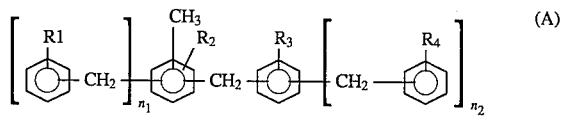

28. The composition of claim 27, wherein the composition comprises at least 60 parts by weight of benzyltoluene, benzylxylene, (methylbenzyl)toluene and (methylbenzyl)xylene per 40 parts by weight of said isomers of formula (A).

29. The composition of claim 28, wherein benzyltoluene comprises at least 30% by weight of said immixture of toluene/xylene compounds.

30. The composition of claim 29, wherein benzyltoluene comprises at least 50% by weight of said immixture of toluene/xylene compounds.

31. The composition of matter, as defined by claim 30, wherein benzyltoluene comprises at least 70% by weight of said immixture of toluene/xylene compounds.

32. The compositions of matter of claim 28, wherein the amount of benzyltoluene, benzylxylene, (methylbenzyl)toluene and (methylbenzyl)xylene ranges from 65 to 90 parts by weight per 35 to 10 parts by weight of isomers of formula (A).

* * * * *